United States Patent
Arabian et al.

(10) Patent No.: US 9,345,590 B2
(45) Date of Patent: May 24, 2016

(54) EQUILIBRIUM SOCKET SYSTEM

(75) Inventors: Adam Arabian, Silverdale, WA (US); David Alan Boone, Seattle, WA (US)

(73) Assignee: Orthocare Innovations LLC, Mountlake Terrace, WA (US)

( * ) Notice: Subject to any disclaimer, the term of this patent is extended or adjusted under 35 U.S.C. 154(b) by 0 days.

(21) Appl. No.: 13/540,368

(22) Filed: Jul. 2, 2012

(65) Prior Publication Data
US 2013/0178950 A1 Jul. 11, 2013

Related U.S. Application Data

(60) Provisional application No. 61/504,073, filed on Jul. 1, 2011.

(51) Int. Cl.

| | | |
|---|---|---|
| *A61F 2/80* | (2006.01) | |
| *A61F 2/60* | (2006.01) | |
| *A61F 2/68* | (2006.01) | |
| *A61L 27/50* | (2006.01) | |
| *A61L 27/56* | (2006.01) | |
| *A61F 2/78* | (2006.01) | |
| *A61F 2/50* | (2006.01) | |
| *A61F 2/70* | (2006.01) | |

(Continued)

(52) U.S. Cl.
CPC . *A61F 2/602* (2013.01); *A61F 2/68* (2013.01); *A61F 2/7843* (2013.01); *A61F 2/80* (2013.01); *A61L 27/50* (2013.01); *A61L 27/56* (2013.01); *A61F 2/7812* (2013.01); *A61F 2002/501* (2013.01); *A61F 2002/5027* (2013.01); *A61F 2002/5032* (2013.01); *A61F 2002/608* (2013.01); *A61F 2002/704* (2013.01); *A61F 2002/742* (2013.01); *A61F 2002/748* (2013.01); *A61F 2002/769* (2013.01); *A61F 2002/7635* (2013.01); *A61F 2002/7655* (2013.01); *A61F 2002/785* (2013.01); *A61F 2002/802* (2013.01); *A61L 2400/16* (2013.01)

(58) Field of Classification Search
CPC A61F 2/7843; A61F 2/7812; A61F 2002/785
USPC .......................................................... 623/34
See application file for complete search history.

(56) References Cited

U.S. PATENT DOCUMENTS

| | | | | |
|---|---|---|---|---|
| 4,252,910 | A * | 2/1981 | Schaefer | 521/145 |
| 4,930,171 | A * | 6/1990 | Frantz | 5/654 |

(Continued)

FOREIGN PATENT DOCUMENTS

WO WO 2009017762 A2 * 2/2009 ............... A61F 2/78

OTHER PUBLICATIONS

International Search Report and Written Opinion mailed Nov. 7, 2012, issued in corresponding International Application No. PCT/US2012/045311, filed Jul. 2, 2012, 9 pages.

(Continued)

*Primary Examiner* — Jacqueline Woznicki
(74) *Attorney, Agent, or Firm* — Christensen O'Connor Johnson Kindness PLLC

(57) ABSTRACT

A prosthesis socket is fitted with a viscoelastic memory material. The material can aspirate a fluid to decrease the interior volume of the socket to compensate for residual limb volume decreases, and fluid can be removed from the viscoelastic memory material to increase the interior volume of the socket to compensate for residual limb volume increases.

15 Claims, 4 Drawing Sheets

(51) Int. Cl.
*A61F 2/74* (2006.01)
*A61F 2/76* (2006.01)

(56) References Cited

U.S. PATENT DOCUMENTS

| | | | |
|---|---|---|---|
| 5,246,464 | A | 9/1993 | Sabolich |
| 5,534,034 | A | 7/1996 | Caspers |
| 5,800,563 | A * | 9/1998 | Arbogast et al. ................ 623/35 |
| 6,149,691 | A | 11/2000 | Fay |
| 7,640,680 | B1 * | 1/2010 | Castro ............................. 36/140 |
| 7,670,386 | B2 | 3/2010 | Ezenwa |
| 7,886,618 | B2 | 2/2011 | Macomber |
| 7,922,774 | B2 | 4/2011 | Macomber |
| 8,111,165 | B2 | 2/2012 | Ortega |
| 8,215,186 | B2 | 7/2012 | Macomber |
| 8,318,820 | B2 * | 11/2012 | Guelcher et al. .............. 521/125 |
| 8,784,708 | B2 * | 7/2014 | Armstrong et al. .......... 264/46.5 |
| 8,883,869 | B2 * | 11/2014 | Schofalvi et al. ............... 521/76 |
| 2002/0099450 | A1 | 7/2002 | Dean, Jr. |
| 2002/0173856 | A1 | 11/2002 | Karason |
| 2003/0078674 | A1 * | 4/2003 | Phillips .......................... 623/37 |
| 2004/0181290 | A1 | 9/2004 | Caspers |
| 2008/0147204 | A1 | 6/2008 | Ezenwa |
| 2009/0281637 | A1 | 11/2009 | Martin |
| 2010/0070051 | A1 | 3/2010 | Carstens |
| 2010/0161077 | A1 | 6/2010 | Boone |
| 2010/0312361 | A1 | 12/2010 | Martin |
| 2011/0160871 | A1 | 6/2011 | Boone |
| 2012/0119912 | A1 | 5/2012 | Ortega |

OTHER PUBLICATIONS

Extended European Search Report mailed Feb. 23, 2015, issued in corresponding European Application No. 12 80 8098.3, filed Jul. 2, 2012, 7 pages.

* cited by examiner

EQUILIBRIUM SOCKET SYSTEM

CROSS-REFERENCE TO RELATED APPLICATION

This application claims the benefit of U.S. Provisional Application No. 61/504,073, filed Jul. 1, 2011, the disclosure of which is fully incorporated herein expressly by reference.

BACKGROUND

Prosthetic limbs have seen many advancements allowing greater functionality. A prosthetic lower limb generally includes a prosthesis socket into which the amputated limb is placed. The fit and comfort of the prosthesis socket will in many instances determine the functionality level of the wearer. If the fit between the prosthesis socket and the limb is not adjusted properly, and is even painful, the prosthesis will see only minimal use. A problem that arises with properly fitting a rigid prosthesis socket to soft human tissue is the variance that occurs in the volume of the living tissue over the course of a day or over a period of days and even weeks. Diurnal, menstrual, and other fluctuations in body weight of the amputee can lead to changes in the volume of the amputated limb, which then affects the fit of the limb to the prosthesis socket. Accordingly, it has been a concern among professionals how to fit or interface living, variable soft tissue to a rigid prosthesis socket.

Prior art sockets are made with a fixed interior volume suited to match the limb volume of the intended wearer. Over time, the wearer may need to replace the socket with a newer socket with a greater or lesser volume. In the interim, the wearer usually makes do by, for example, stuffing the socket with socks, sponges, and the like.

In U.S. Patent Application Publication No. US 2009/0281637 A1, herein incorporated by reference in its entirety, the assignee of the present application sought to address this concern by providing a vacuum system in a prosthetic limb. This publication discloses the evacuation of air from spaces existing within the socket that results in a secure fit and improved suspension of the residual limb in the socket. Notwithstanding this improvement, there is a continuing need to improve the fit of a prosthesis socket and thereby, raise the functionality level of the wearer.

SUMMARY

A first embodiment is related to a method of compensating for variations in volume of a residual limb within a prosthesis socket. The method includes aspirating a compressible fluid into a viscoelastic memory material within an interior of a socket when a residual limb decreases in volume within the socket, wherein, as the viscoelastic memory is filled with the fluid, the viscoelastic memory material expands to compensate for the volume decrease in the residual limb.

In the method, the viscoelastic memory material may expand to create vacuum within the viscoelastic memory material to draw the compressible fluid within the viscoelastic memory material as the residual limb decreases.

The method may further include withdrawing the compressible fluid from the viscoelastic memory material when the residual limb volume increases within the socket.

In the method, a vacuum may be created external to the viscoelastic memory material to withdraw the compressible fluid from the viscoelastic memory material The method may further include sensing a pressure experienced by the viscoelastic memory material and maintaining the sensed pressure within a range between a low pressure target and high pressure target.

The method may further include, when the sensed pressure is below the low pressure target, aspirating a fluid into the viscoelastic memory material and increasing the volume of the viscoelastic memory material until the sensed pressure is above the low pressure target.

The method may further include, when the sensed pressure is above the high pressure target, removing a fluid from the viscoelastic memory material and decreasing the volume of the viscoelastic memory material until the sensed pressure is below the high pressure target.

The method may further include sensing a pressure experienced by the viscoelastic memory material, correlating the sensed pressure to a correlated size of the viscoelastic memory material, comparing the correlated size of the viscoelastic memory material to a size target, and when the correlated size is less than the size target, aspirating a fluid into the viscoelastic memory material to increase the size of the viscoelastic memory material.

The method may further include aspirating fluid through a conduit open to atmospheric air.

The method may further include sensing a pressure experienced by the viscoelastic memory material, correlating the sensed pressure to a correlated size of the viscoelastic memory material, comparing the correlated size of the viscoelastic memory material to a size target, and, when the correlated size is greater than the size target, removing a fluid from the viscoelastic memory material to decrease the size of the viscoelastic memory material.

The method may further include operating a vacuum pump connected to the viscoelastic memory material to remove the fluid from the viscoelastic memory material.

The method may further include sensing a pressure experienced by the viscoelastic memory material and, when the sensed pressure is below a low pressure target caused by swinging the prosthesis during a swing phase of walking, delaying aspirating a fluid into the viscoelastic memory material.

The method may further include sensing a pressure experienced by the viscoelastic memory material and, when the sensed pressure is above a high pressure target caused by standing on the prosthesis during a stance phase of walking following a swing phase, delaying removing a fluid from the viscoelastic memory material.

In the method, the viscoelastic memory material may include an open cell structure, and have a transition temperature between a fully firm state and an alternate soft state that is at or above normal body temperature.

In the method, the viscoelastic memory material may have predetermined time for rebound after compression that is at least one second.

The method may further include sensing a pressure within an interior of the socket, and maintaining the sensed pressure between a low pressure target and a high pressure target.

A second embodiment can be a prosthesis. The prosthesis includes a socket defining an interior available volume, wherein the socket has an opening for receiving a residual limb. The prosthesis includes a viscoelastic memory material placed on the socket, wherein the viscoelastic memory material is configured to create a vacuum to aspirate a compressible fluid from outside the viscoelastic memory material and decrease the available volume within the socket. The prosthesis may include a pump connected to the viscoelastic memory material, wherein the pump is configured to create a vacuum to withdraw the compressible fluid from within the viscoelastic memory material and increase the available volume within the socket.

In the prosthesis, the viscoelastic memory material may be placed on a side wall of the socket.

The prosthesis may further include a pressure sensor configured to measure the pressure experienced by the viscoelastic memory material.

The prosthesis may further include a vent connected to the viscoelastic memory material, wherein the vent is configured to connect the viscoelastic memory material to atmospheric air.

In the prosthesis, the viscoelastic memory material may include an open-cell foam.

The prosthesis may further include a storage unit having a correlation table that correlates a pressure to a volume of the viscoelastic memory material.

The prosthesis may further include a storage unit having a correlation table that correlates a pressure to a volume of the viscoelastic memory material for a time of a day.

In the prosthesis, the viscoelastic memory material has a transition temperature between a firm state and a soft state that is at or above a normal human body temperature.

In the prosthesis, the viscoelastic memory material may be placed at a rear wall of the socket.

The prosthesis may further include an impermeable barrier between the viscoelastic memory material and the interior of the socket.

In the prosthesis, the impermeable barrier may be a skin formed from the viscoelastic memory material.

In the prosthesis, the impermeable barrier is an elastic material.

The prosthesis may further include more than one viscoelastic memory materials, each viscoelastic memory material being placed at a different location on the socket.

The prosthesis may further include a central processing unit configured to operate the pump, wherein the central processing unit is programmed to receive a sensed pressure, correlate a volume of the viscoelastic memory material based on the sensed pressure, determine whether the correlated volume is above or below a predetermined volume, calculate a volume difference required to achieve the predetermined volume, and command aspiration of the viscoelastic memory material when the correlated volume is below the predetermined volume, and command a pressure decrease of the viscoelastic memory material when the correlated volume is above the predetermined volume.

In the prosthesis, the pump may be further connected to the interior of the socket, and the pump is configured to maintain a pressure within the interior of the socket and maintain a pressure within the viscoelastic memory material.

In the prosthesis, the viscoelastic memory material is provided in a projection provided in the socket.

In the prosthesis, an opening may be provided in the sidewall of the prosthesis, a cassette configured to the shape of the viscoelastic memory material is provided over the opening and forms the sidewall of the socket, and the viscoelastic memory material is provided within the cassette.

The prosthesis may further include an adaptor, a prosthetic foot, and a pylon, wherein the adaptor is rigidly attached to a base of the socket, the pump is configured to receive the adaptor at an interface configured to allow angulation of the adaptor to align the socket to a remainder of the prosthesis, and the pump is connected to a prosthetic foot via the pylon.

A third embodiment is also related to a prosthesis. The prosthesis may include a socket defining an interior available volume with an opening for receiving a residual limb, a viscoelastic memory material placed on the socket, wherein the viscoelastic memory material is configured to expand to reduce the available volume within the socket, and the viscoelastic memory material is in communication with ambient atmospheric pressure.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
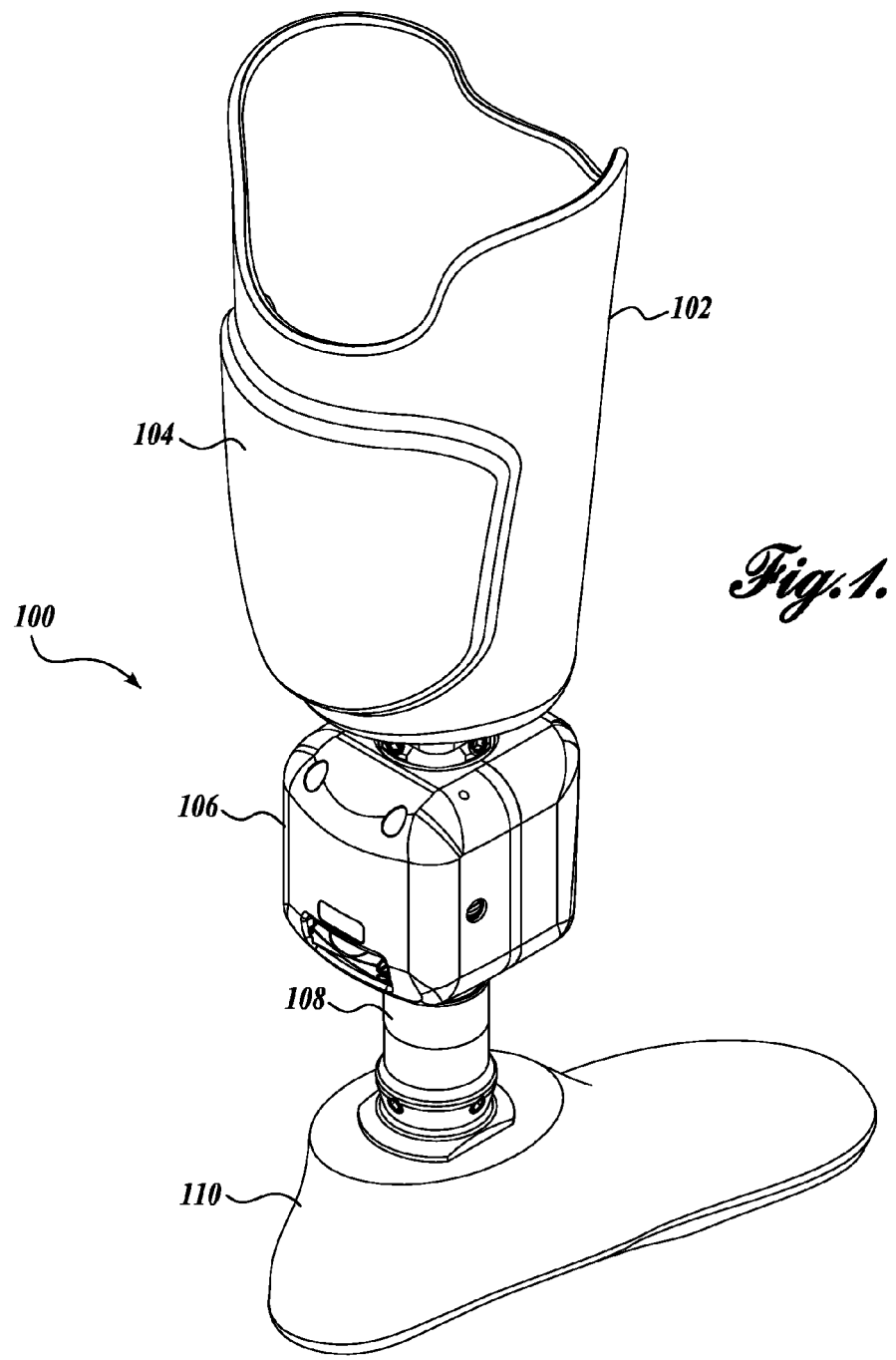
FIG. 1 is a diagrammatical illustration of a prosthesis with a socket having a volume compensation element on the socket.

Referring to FIG. 1, a prosthesis 100 for a lower limb amputee is illustrated. The prosthesis 100 includes a socket 102 with at least one volume compensation element 104 on the socket 102. The volume compensation element 104 allows the volume that is available inside of the socket to vary in accordance with changes in the volume of the residual limb. The prosthesis 100 includes a pump 106 connected to the socket 102 at a lower end thereof. The pump 106 is connected to a pylon 108 on a lower end of the pump 106. The lower end of the pylon 108 is connected to the upper portion of a foot 110. The prosthesis socket 102 is a cup-shaped device to receive an amputated limb. The upper end of the socket 102 is open to allow the placement of the amputated limb (i.e., also referred to as the residual limb). The socket 102 is usually manufactured specifically for the wearer and may be fitted to any kind of lower limb amputee, including, but not limited to, a transtibial amputee or a transfemoral amputee.

While a lower limb prosthesis is used to illustrate representative embodiments of the invention, the methods and devices disclosed herein are not thereby limited solely for use on lower limb prosthesis devices. The volume compensation element 104 and methods disclosed herein may be applicable to a multitude of other uses.

The prosthesis socket 102 serves as the physical connection between the user's body and the prosthesis 100. The functionality and comfort of the prosthesis 100 is to a great degree determined by the intimacy of the connection. Changes in the volume of the residual limb lead to a poor match between the residual limb and the prosthesis socket 102. With precise matching of the socket 102 volume to the residual limb volume, hydrostatic forces become key to residual limb support within the socket 102. Fluctuations in body volume, either normal or induced pharmacologically or by disease, can lead to changes in fit that negatively influence limb health, comfort, and the ability to successfully ambulate. Throughout the day, week, and even months, it is common for residual limb volume to change and to be noticeable to prosthesis users. Volume typically decreases due to the forces on the residual limb from ambulation, causing venous return of fluid out of the tissue. Limb volume can change sufficiently to create problems for the user within the course of a day. Volume decrease throughout the day will cause the residual limb to slip deeper into the socket 102. Changes in residual limb volume may occur unevenly across the tissue with soft tissue being responsible for the majority of the loss. With the loss not occurring uniformly, treatment of a specific area of the limb would be advantageous. Long-term changes in residual limb volume may be the result of a number of factors. Pharmaceuticals often used in conjunction with amputation, such as chemotherapy drugs and diuretics, can lead to significant fluctuations in tissue fluid volume. Also, immediately post-amputation, the residual limb will normally experience large changes in volume and shape. The tissue, traumatized by amputation, will first swell, but over weeks and months, the swelling lessens, accompanied by loss of muscle mass as the unused muscles atrophy. A common long-term factor which affects residual limb volume is change in overall body weight. Weight fluctuations can present a significant problem. A small percentage of weight gain or loss can make the prosthesis socket fit drastically different. If the person was active prior to amputation, there is often a decrease in physical activity, resulting in weight gain. Conversely, if the amputation is a result of chronic pain that had served as a mobility limiting factor, it may lead to an increase in activity and, thus, a reduction in weight and corresponding limb volume. After the period of post-amputation changes, most commonly there is a slow increase in weight and limb volume. This results in the socket being too tight, resulting in increased pressure at certain points, or too loose, resulting in slippage, friction, and uneven force distribution. Both result in a need for a new socket to be built which is often a labor-intensive and costly procedure.

Disclosed herein is a system and a method for accommodating the residual limb volume changes discussed above through the use of at least one volume compensation element 104 on the socket 102. The volume compensation element 104 is used to reduce increase the available volume inside the socket 102 selectively. In some embodiments, the volume compensation element 104 may be coupled to a vacuum pump to evacuate a compressible fluid, such as air or other fluid, from within the volume compensation element 104, or in other embodiments, the volume compensation element 104 may be used without a vacuum pump. Further, a socket 102 may be fitted with more than one volume compensation element 104 at different locations on the socket 102. The locations may correspond to areas of the amputated limb that are more likely to see variations in volume. Additionally, the socket 102 may include the use of both the volume compensation element 104 and the application of vacuum to the interior of the socket 102 via a vacuum pump. The vacuum pump may control the pressure within the volume compensation element and the socket proper, intermittently, or at the same time, or the pump may control the pressure in one and then the other.

Illustrated in FIG. 1 is a volume compensation element 104 placed, in one embodiment, at the rear of the socket 102 on the side of the heel. The volume compensation element 104 can be placed on the socket 102 to coincide with soft tissue or muscle. The volume compensation element 104 may use a viscoelastic memory material 122. The viscoelastic memory material 122 may be an open-celled foam with memory. The volume compensation element 104 including the viscoelastic memory material 122 can be placed on the socket 102 to make contact with the soft tissue areas of the residual limb, because such tissues are most likely to lose volume. In one embodiment, the volume compensation element 104 including the viscoelastic memory material 122 can be placed such that it will lie against the triceps surae muscle (calf muscle). In this way, the socket fit around the hard tissue areas that provide control and support, such as the lateral and medial aspects of the tibia, remain static. These non-volume adjusting areas will serve as anatomical anchors for the socket 102 with expansion of the volume compensation element 104 or elements acting to maintain position of the limb in the socket 102 and accommodate for the space left by any volume loss of the residual limb, thus maintaining the integrity of the fit of the socket 102. It is to be understood that volume compensation element 104 can be placed at any location on the socket 102. In other embodiments, a plurality of volume compensation elements 104 can be placed on the socket 102 at different locations. For example, a volume compensation element can be placed at the rear and front or at the medial or lateral side of the socket 102. Further still, a volume compensation element 104 can be placed at or near the floor or bottom of the socket 102.

Figure 2:
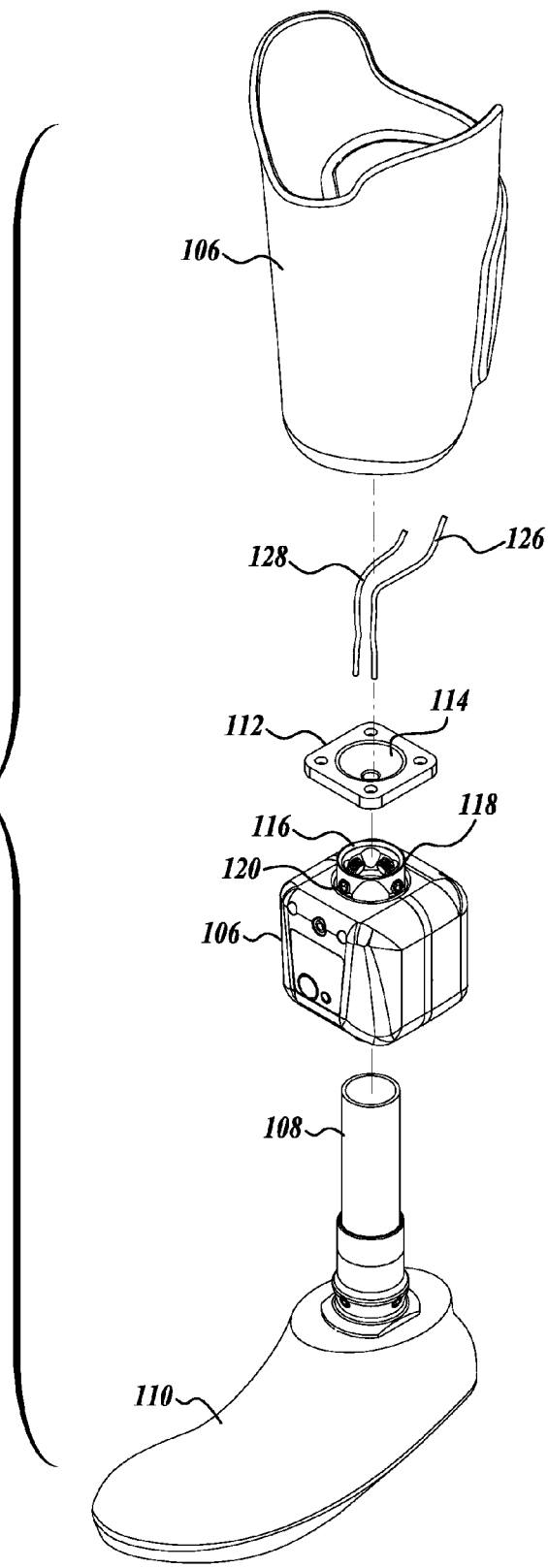
FIG. 2 is a diagrammatical illustration of an exploded view of the prosthesis of FIG. 1.

As illustrated in FIG. 2, the prosthesis socket 102 is connected to the pump 106 via a pyramid adaptor 112. The pyramid adaptor 112 is rigidly attached by its base 112 to the base of the socket 102 via fasteners (not shown). The pyramid adaptor 112 includes a four sided protuberance (resembling an inverted pyramid) projecting downwardly from a convex hemispherical surface 114 (when seen from below). The protuberance fits within a collar 118 of the pump 106. The collar 118 further has holes for set screws 120 to press against the four sides of the pyramid adaptor 112 and thus secure the pyramid adaptor 112 to the pump 106. In the case where no pump is used, the pyramid adaptor 112 may connect directly to the pylon 108 fitted with a collar 118. The collar 118 is provided with a concave hemispherical surface 116 that supports the convex surface 114 and allows angulation of the socket 102 in relation to the pump 106 in the forward/rear and medial/lateral directions. Thus, the socket 102 can be geometrically adjusted with respect to the remainder of the prosthesis 100. While a pyramid adaptor can be used, other adaptors are also possible. This spatial adjustment to align the socket 102 can be performed using a sensor and methods disclosed in the applicants' prior applications. A method for geometrically aligning a prosthesis socket is described in the applicants' prior publications, including U.S. Patent Application Publication No. 2008/0140221, which is fully incorporated herein in its entirety by reference.

The bottom side of the pump 106 may include a clamp (not shown) that fits on the outer diameter at the top of the pylon 108, which in turn is connected to the prosthetic foot 110.

As illustrated in FIG. 2, the pump 106 is connected via first 126 and second 128 conduits, such as tubing, provided between the pump 106 and the socket 102. The first conduit 126 connects the vacuum producing means of pump 106 to the volume compensation element 104. Specifically, the conduit 126 is connected to an airtight enclosed space containing the viscoelastic memory material. The second conduit 128 connects the vacuum producing means of the pump 106 to the inside of the socket 102. The conduit 128 does not connect to the viscoelastic memory material. More specifically, the socket 102 may include an air impermeable membrane 150 (seen in FIG. 3) that is provided within the interior of the socket 102 and lines the interior of the socket 102. The membrane 150 seals the socket 102 against a residual limb. The conduit 128 is provided within the socket 102 so as to evacuate the air within any spaces that occur between the residual limb and the membrane 150.

Figure 3:
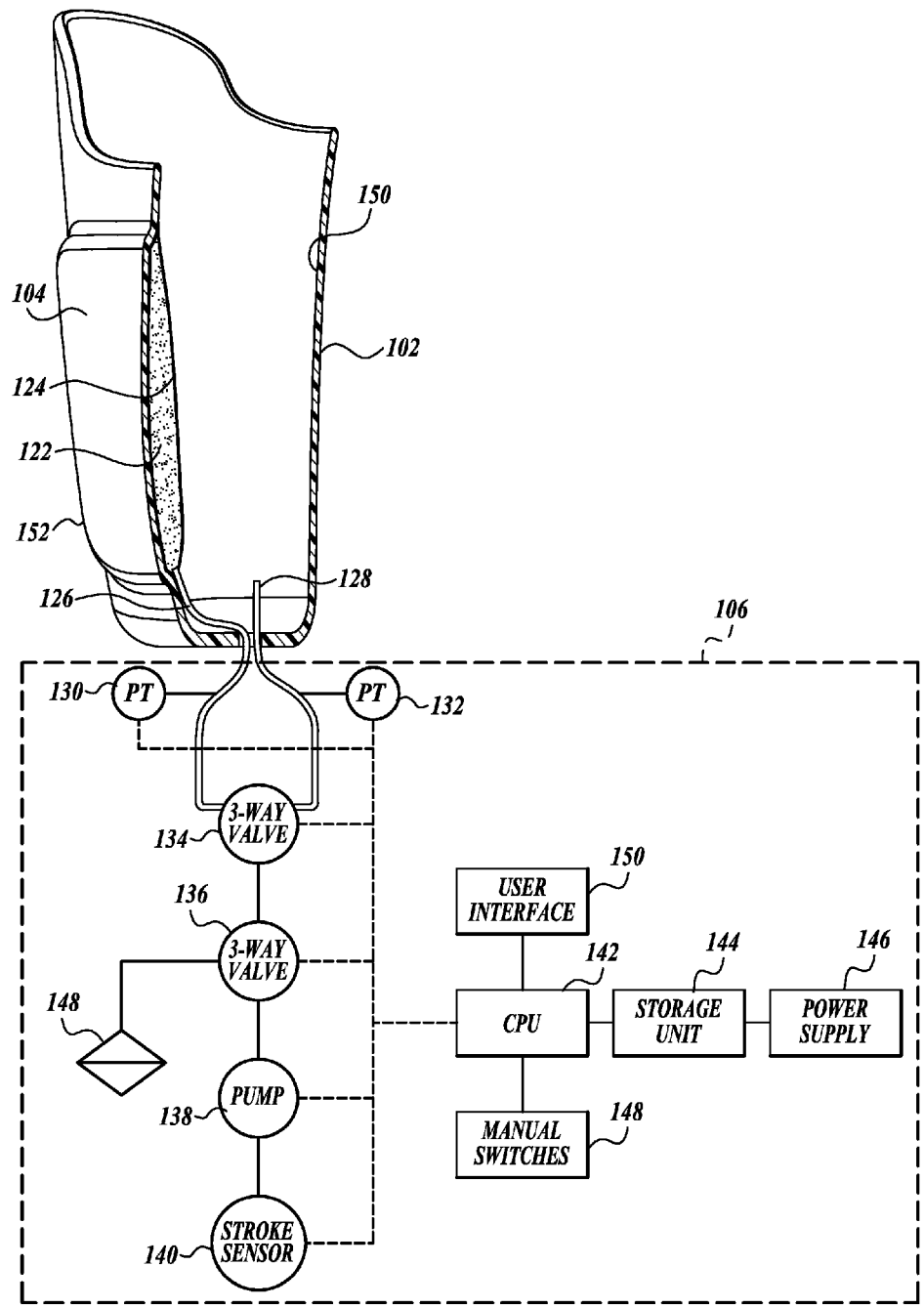
FIG. 3 is a schematic illustration of the socket with a volume compensation element and pump of the prosthesis of FIG. 1.

Referring to FIG. 3, a schematic diagram is illustrated showing the components of pump 106 (delineated by a broken line) for performing volume compensation using the volume compensation element 104 and low-pressure suspension of the socket 102. As used herein, low-pressure suspension refers to applying vacuum inside the socket 102 other than at the volume compensating element 104 to maintain a fit, or contact, of the residual limb to the membrane 150.

In the illustrated embodiment, the interior of the socket 102 is connected to the pump 106 via conduit 128. The socket 102 may have the membrane 150 covering the inside of the socket 102 so as to seal against the skin of the residual limb. The conduit 128 penetrates the membrane 150 and allows evacuation of the spaces between the membrane 150 and residual limb. In other embodiments, the membrane 150 may be omitted. A vacuum may be applied inside of the socket 102 to maintain suspension of the residual limb 102 in the socket 102. As used herein, pressure includes vacuum, which is simply a pressure lower than the prevailing atmospheric pressure. The control of pressure and/or vacuum for suspension of the residual limb within the socket 102 has been discussed in the applicant's prior U.S. Patent Application Publication No. 2010/0312361 A1, incorporated herein in its entirety by reference. In prosthetics, "suspension" is a term that means adhering the residual limb to the socket, for example, to keep the prosthesis in place.

In the illustrated embodiment, the pump 106 may include a pressure sensor 132 for monitoring and/or measuring the pressure inside of the socket 102, specifically, the pressure (vacuum) in the area between the residual limb, and membrane 150 (if provided). Such pressure is used for control of low-vacuum suspension. The pressure sensor 132 may indicate the absolute pressure, gauge pressure (i.e., the pressure above atmospheric pressure), or a differential pressure (a difference of any two pressures). While low-vacuum suspension can be successful at compensating for volume changes of the residual limb, the socket 102 disclosed herein may also include a volume compensation element 104. The volume compensation element 104 changes the available volume within the socket 102 by expanding and contracting. Specifically, the viscoelastic memory material is allowed to expand to fill in available volume in the socket caused by a decrease in the volume of the residual limb and is compressed to free up available volume in the socket to accommodate an increase in the volume of the residual limb. The natural tendency of the viscoelastic memory material is to expand to return to its normal, natural state, while compression is assisted by the use of a vacuum pump.

The volume compensation element 104 may be used with low-vacuum suspension. Alternatively, the volume compensation element 104 can be used alone for compensating volume changes within the socket 102.

The viscoelastic memory material 122 is connected to the pump 106 via conduit 126. The viscoelastic memory material 122 comprises an open-celled structure that allows the material 122 to expel a fluid when compressed, or to aspirate a fluid into the material 122 when under little or no external compression. In one embodiment, the fluid is a compressible fluid, such as air. As the material 122 expands, the material 122 aspirates, or takes in, the fluid due to its memory properties tending to return the material to its original shape. In one embodiment, the fluid that is expelled and aspirated by the viscoelastic memory material 122 is air. The viscoelastic memory material 122 may be surrounded by an impermeable barrier 124 to sustain pressure therein. The barrier 124 may surround the viscoelastic memory material 122 on all surfaces, or the barrier 124 may cover only so much of the viscoelastic memory material 122 that is exposed to the interior of the socket 102. The impermeable barrier 124 may be a solid, non-cellular skin formed on the outer surface of the viscoelastic memory material 122, which is formed of the same material at the cellular structure, or the impermeable barrier 124 may be a separate and distinct material, such as a silicone sheet or pouch or other elastic material, as described below, that encloses the viscoelastic memory material 122 in an air-tight condition.

The opening of the conduit 126 is in communication with the viscoelastic memory material 122, and the cellular structure, within the impermeable barrier 124. The conduit 126 is used for removing a fluid within the open-celled structure of the viscoelastic memory material 122 to compress the material, or when the material is already compressed, a fluid is aspirated into the material 122 through the conduit 126 so that the material 122 attempts to resume its normal (uncompressed) state. It is to be appreciated that when the residual limb within the socket 102 is pressing against the viscoelastic memory material 122, the material 122 can only assume so much of its uncompressed state or shape that balances the pressure exerted on it by the residual limb.

In the illustrated embodiment, the removal of a fluid from the viscoelastic memory material 122 to compress the material (and permit greater volume in the socket 102) is via a mechanical device, such as the pump 106, which can be a reciprocating vacuum pump, and aspiration of the fluid into the viscoelastic memory material 122 is unassisted by mechanical devices, and occurs when pressure against the material 122 is reduced, such as by contraction of the residual limb volume. In the latter case, the natural tendency of the viscoelastic memory material 122 to return to its uncompressed state is the cause for the aspiration of the fluid.

In another embodiment, the removal of fluid from within the viscoelastic memory material 122 occurs from the application of pressure of the residual limb against the viscoelastic memory material 122, and aspiration of the fluid occurs when the pressure is reduced (through contraction of the residual limb volume), and the natural tendency of the viscoelastic memory material 122 to return to its uncompressed state is the cause for the aspiration of the fluid. Thus, in the embodiment just described, a mechanical device, such as pump 106, to compress the viscoelastic memory material 122 may not be necessary.

The pump 106 may include a pressure sensor 130 for measuring or sensing the pressure experienced by the viscoelastic memory material 122. The pressure sensor 130 may indicate the absolute pressure, gauge pressure (i.e., the pressure above atmospheric pressure), or a differential pressure (a difference of any two pressures). The pressure sensor 130 may be used to decide whether to compress or aspirate the viscoelastic memory material 122.

In one embodiment, the pump 106 is provided to control the volume compensation element 104 and the low-vacuum suspension system of the socket 102. The pump 106 may be constructed so that both the viscoelastic memory material 122 and the internal volume of the socket 102 are connected to a vacuum-producing element, such as a reciprocating piston, and so that both the viscoelastic memory material 122 and the internal volume of the socket 102 can be subjected to a vacuum. Additionally, the pump 106 may be constructed so that the viscoelastic memory material 122 and the socket 102 may be subjected to atmospheric pressure so as to allow aspiration of air to either the volume compensation element 104 or to the socket 102 interior or both. In the illustrated embodiment, a pair of three-way valves 134 and 136 may be used to connect either the viscoelastic memory material 122 or the socket 102, or both, to a vacuum-producing element 140 (VPE) and to a vent 148 to atmosphere. However, other configurations may include two vacuum pumps and two vents to atmosphere, one for each of the viscoelastic memory material 122 and for the socket 102, or a pump with more than one vacuum-producing element incorporated into one pump. Instead of 3-way valves, single-port valves may be used. In some embodiments, the control of vacuum in the viscoelastic memory material 122 and the socket 102, is practiced intermittently. For example, the system controls the vacuum in the viscoelastic memory material 122, followed by the vacuum in the socket 102, and this cycle is repeated. In other embodiments, if two VPEs are provided, the control of vacuum in the viscoelastic memory material 122 and the socket 102, may be simultaneous. However, other combinations are possible.

In the illustrated embodiment, both the conduit 128 from the internal volume of the socket 102 and the conduit 126 from the viscoelastic memory material 122 are connected to three-way valve 134. The three-way valve 134 may include a plug that can rotate to connect one of conduits 126 or 128 to the second three-way valve 136. The three-way valve 136 connects whichever of the conduits is selected by the three-way valve 134 to either of the vacuum-producing element 138 or to an atmospheric vent 148. The three-way valve 136 may include a plug that can rotate to either of the vacuum-producing element 138 or the atmospheric vent 148. Vacuum-producing element 138 can be any device used to apply a vacuum. For example, vacuum-producing element 138 can be a reciprocating piston pump. The vacuum-producing element 138 may include a stroke sensor 140. The stroke sensor 140 is an instrument that counts the number of strokes taken by the vacuum-producing element 138 after it has started or during a preselected time period.

The three-way valves 134 and 136 can be automatically or manually selected to one of the conduits 126 and 128 and to one of the vacuum pump 138 or to the vent 148. The three-way valves 126 and 128 may include instrumentation, including position sensors and electrically or pneumatically driven actuators. Actuators move the valve plugs to the desired orientation. Position sensors indicate the position of the valve to determine how the valve is configured, i.e., whether the vacuum compensation element 104 or the socket 102 are configured to the vacuum-producing element 138 or the atmospheric vent 148. The instruments provide data to a central processing unit 142, which makes decisions based on the data, including positions of valves 134 and 136, and the pressures 130, and 132.

When the vacuum-producing element 138 is a piston, the stroke sensor 138 is provided to maintain and keep track of the number of piston strokes per unit of time. The pressure sensors 130 and 132, the first and second three-way valves 134 and 136, the vacuum-producing element 138, and the stroke sensor 140 may provide inputs to and be under the control of the central processing unit 142. The central processing unit 142 can receive a number of inputs, such as the pressure (or vacuum) experienced within the socket 102, the pressure (or vacuum) experienced by the viscoelastic memory material 122, the position of the three-way valve 134, the position of the three-way valve 136, the on/off state of vacuum-producing element 138, and the number of strokes completed by the vacuum-producing element 138.

The central processing unit 142 is connected to a storage unit 144. The storage unit 144 may contain algorithms that decide a strategy for maintaining the pressure within the socket 102, compensate for volume using the viscoelastic memory material 122, or both. The storage unit 144 can be provided in the form of memory, such as ROM, and other well known storage units for computers. The pump 106 includes a power supply 146, such as a battery. The power supply 146 may be connected to a bus that is further connected to all instrumentation or electrically driven devices. In one embodiment, the electrical system is powered using low voltage employing less than 18 volts without the use of capacitors of significant size, to avoid risk of any electrical shock or injury to the wearer.

Additionally, the pump 106 may include one or more manual switches 148. For example, a manual switch can be provided to activate the vacuum-producing element 138 to apply more vacuum within the socket 102 for greater suspension. Additionally, or alternatively, a second manual switch can be provided to operate the vacuum-producing element 138 to remove fluid from the viscoelastic memory material 122, thus compressing the material 122 and allowing greater volume within the interior of the socket 102. When a manual switch is turned on to activate vacuum to either the interior socket, or the volume compensation element, the 3-way valves 136, 138, may be configured automatically. Additionally, or alternatively, a manual switch can be used as a selector switch to configure the three-way valves 136 and 138 to the atmospheric vent 148 or to the vacuum pump 138. The switches can be two or three position switches, such that in one position, the valves 134 and 136 are aligned to vacuum pump 138, and in a second position, the valves will align to the atmospheric vent 148. One of this type of switch can be provided to manually operate both the vacuum compensation element 104, and the socket 102 pressure. As just described, operation of the vacuum compensation element 104 and socket 102 pressure can rely solely on manually operated switches. Decisions whether to operate the low-pressure socket suspension, or the volume compensation element can be left to the user/wearer. Other modes may use instruments to automatically operate and control the volume compensation element 104 and the socket 102 pressure according to a set of algorithms, and still other embodiments may use both manually operated switches with a degree of intelligent control.

The pressure/vacuum within the interior socket 102 can be based on a pressure measurement provided by pressure sensor 132, and the volume compensation element 104 including the viscoelastic memory material 122 can be controlled based on a pressure/vacuum measurement provided by pressure sensor 130. A suitable algorithm can rely on simply a low pressure target and a high pressure target with a goal of maintaining the sensed pressure within the low and high pressure targets. However, other algorithms may be more complex and use pressure as a means of correlating pressure to volume. For example, a pressure correlation table of the pressure of the viscoelastic memory material 122 versus the volume of the viscoelastic memory material 122 can be created through user trials. The correlation table can then be used in algorithms to indirectly control the volume of the viscoelastic memory material 122 through directly controlling the pressure in the viscoelastic memory material 122.

The algorithms controlling the operation of vacuum-producing element 138 and valves 136 and 138 that ultimately result in the pressure and thus, volume, of the viscoelastic memory material 122 may be described in the context of computer-executable instructions executed by the central processing unit 142. Any steps of algorithms described herein may be interchangeable or combined with other steps, or be arranged in a different sequence in order to achieve the same result. Such algorithms can be stored in a tangible form, such as ROM, RAM, CD, or other storage media.

FIG. 3 illustrates the pump 106 including the central processing unit 142, and a storage unit or memory 144. The storage unit 144 stores the algorithms for controlling the operation of the vacuum-producing element 138 and valves 134 and 136. The storage unit 144 generally comprises memory, such as Random Access Memory ("RAM"), Read-Only Memory ("ROM"), flash memory, and the like.

The storage unit 144 can store program code that provides a method for controlling the viscoelastic memory material 122. The volume compensation element 104 can be regulated by an algorithm configured to operate the vacuum-producing element 138 and valves 134 and 136. For example, as the residual limb volume decreases throughout the course of the day and the available volume within the socket increases, the valves 134 and 136 may be configured to connect the viscoelastic memory material 122 to the vent 148 on a predetermined schedule and for a predetermined period of time. This allows the viscoelastic memory material 122 to take in air to make up for the volume decrease of the residual limb and fill in the available volume within the socket 102. Conversely, when the valves 136 and 138 are configured to perform vacuum suspension of the socket 102 and a high pressure is sensed in the viscoelastic memory material 122, the valves 134 and 136 may be reconfigured to allow vacuum-producing element 138 to lower the pressure to withdraw fluid, compressing the viscoelastic memory material 122 and making available more volume within the socket. Thus, the viscoelastic memory material 122 can be made to expand or compress throughout the day to maintain the socket fit and reduce sheer forces.

In another embodiment, the viscoelastic memory material 122 can be continuously in communication with atmospheric pressure, and, therefore, when the residual limb volume decreases, the viscoelastic memory material is free to aspirate in air, and when the viscoelastic memory material 122 is under compression that exceeds the natural stiffness of the material, the viscoelastic memory material 122 is free to expel air. Such embodiment does not rely on a vacuum-producing element, and can be implemented without valves.

Figure 4:
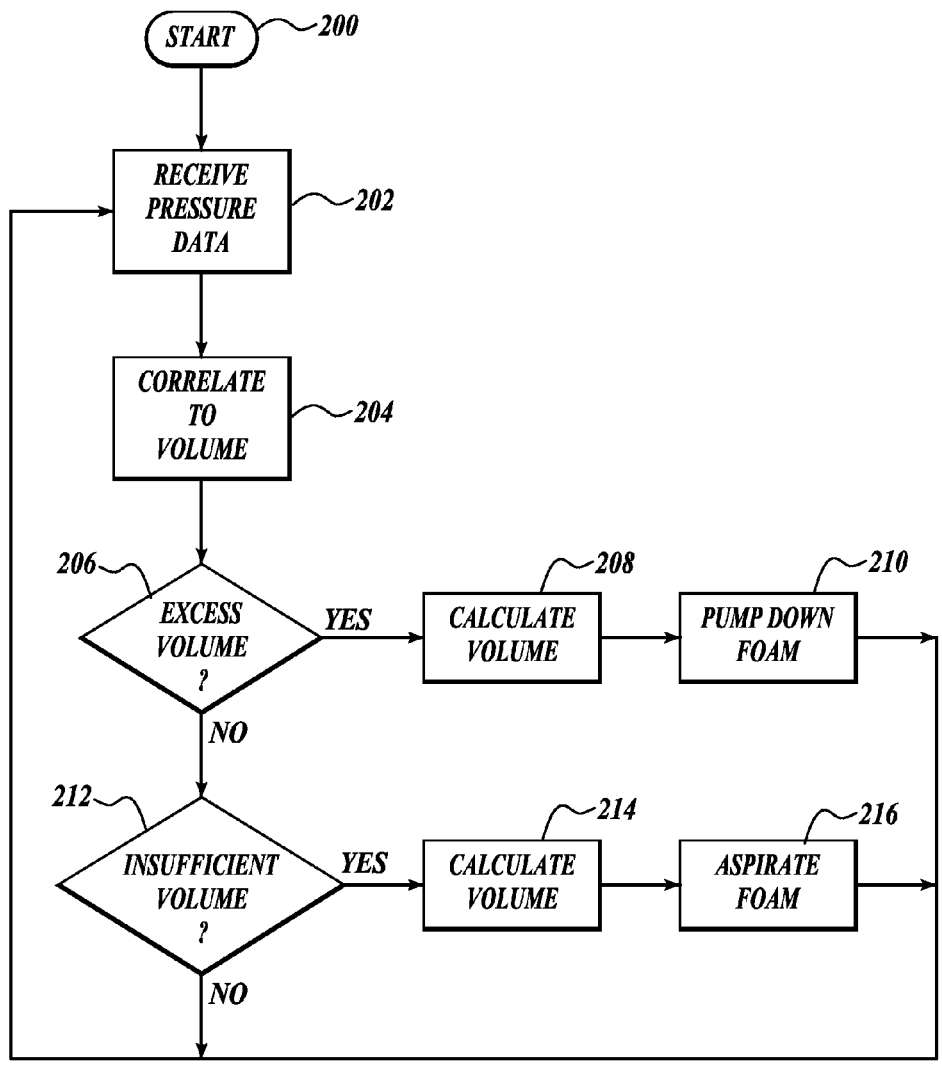
FIG. 4 is a flow diagram of one embodiment of a method for performing volume compensation of the socket.

Referring to FIG. 4, a flow diagram of one embodiment of a method of automatically adjusting the volume of the viscoelastic memory material 122 is illustrated. It is to be appreciated that variations from the illustrated method are possible as described herein, and the embodiments are not limited to the one depicted. The method begins with block 200. From block 200, the method enters block 202. In block 202, the method receives pressure data of the pressure of the viscoelastic memory material 122. Pressure data can be in the form of an instantaneous pressure from pressure sensor 130 that measures the pressure experienced by the viscoelastic memory material 122. Alternatively, the pressure collected over a predefined time period may be collected and averaged. In still another alternative, the pressure can be a rolling average pressure. An averaged pressure or a rolling average pressure avoids spikes in pressure that may cause wide swings in the operation of the system. For example, each time a wearer steps on the prosthesis, the viscoelastic memory material 122 may experience a sharp increase in pressure, while the moment the wearer lifts the prosthesis at the start of the swing phase during normal walking, the viscoelastic memory material 122 may experience a decrease in pressure.

From block 202, the method enters block 204. In block 204, the pressure is correlated to a volume of the viscoelastic memory material 122. The volume of the viscoelastic memory material 122 can be determined by initially performing data-gathering trials to build a correlation table that relates a size, such as volume or thickness of the viscoelastic memory material 122 to the sensed pressure. For example, to collect data initially, a wearer of a prosthesis with the volume compensation element 104 can be allowed to control the volume of the viscoelastic memory material 122 so that pressure versus volume data can be gathered for a time period of one day over the course of several days. The data collected can be used to determine trends in the data. For example, the rate of volume decrease or increase over the course of the day. The specific volume at a particular time of day can be known and stored as one or more correlation tables in the storage unit 144. In one particular algorithm, the system senses the time of day, correlates the time of day to a particular volume. A correlation table that has stored therein the pressure correlating to a particular volume for a particular time of day can be stored in the storage unit 144 of the pump 106 and accessed by the CPU 142. The CPU 142 has a clock that indicates the time of day and knows the pressure correlating to volume that needs to be achieved at that time of day.

From block 204, the method enters decision block 206. After determining the correlated volume from the pressure of the viscoelastic memory material 122 using a correlation table, the method compares the correlated viscoelastic memory material volume to a predetermined volume. The predetermined volume is the volume that was measured during the trial period at a particular time of day, for example, and is the volume that should be achieved. The predetermined volume can be an average, a minimum, or a maximum, or another, representative volume of the viscoelastic memory material. In one embodiment, the predetermined volume can be set to a different value corresponding to a different time of the day. If the method determines that the correlated volume is greater than the predetermined volume, the method calculates the excess or difference in volume between the correlated volume and the predetermined volume in block 208, and then performs removal of air from the viscoelastic memory material 122 in block 210 by starting the vacuum-producing element 138. As the vacuum-producing element 138 is operating, the pressure may continue to be sensed to determine when the condition of excess volume is no longer true. Alternatively, in one embodiment, a correlation table can be built that correlates a volume decrease amount based on the number of strokes. In this case, the central processing unit 142 may receive the number of strokes that is calculated to reduce the volume of the viscoelastic memory material 122 to reach the predetermined volume without any feedback of pressure.

If the excess volume condition in block 206 is not true, the method enters decision block 212. In block 212, the method determines whether the viscoelastic memory material 122 has insufficient volume compared to the predetermined volume. If the determination in block 212 is that the correlated volume is insufficient compared to the predetermined volume, the method calculates the difference between the predetermined volume and the correlated volume and performs aspiration of the viscoelastic memory material 122 in block 216. Aspiration refers to opening the vent 148 to expose the viscoelastic memory material 122 to atmospheric air for a specific time. This has the result that the viscoelastic memory material 122 may expand in accordance with its natural resilient properties to make up the volume that is lacking. From both blocks 210 and 216, the method returns to block 202 to continue sensing pressure and continuously make adjustments in the volume.

While one specific embodiment for a control algorithm has been described, the invention is not thereby limited. The system described herein can include modifications or alternatives to the steps described above that are within the spirit and scope of the invention. For example, instead of correlating pressure to volume, the sensed pressure may be used directly or indirectly to make decisions to compress or expand the volume compensation element. For example, the pressure of the compensation element can be sensed continuously, or semi-continuously, one or more pressure measurements can be averaged, and the pressure average may be compared to a predetermined pressure, obtained during the data training period. Whether the averaged pressure is above or below the predetermined pressure will determine whether the volume compensation element is allowed to aspirate in air to increase volume or to reduce volume by operating the vacuum-producing element.

Furthermore, the wearer may simply override any algorithms and either control the volume increase and decrease in the viscoelastic memory material.

The method illustrated in FIG. 4 is described with reference to controlling the volume of the volume compensation element 104. However, the pressure of the interior of the socket 102 may be controlled by the pump 106, when the pump 106 is not controlling the volume of the volume compensation element 104. In this case, the pump 106 would normally look to the pressure of the socket 102 sensed by the pressure sensor 132. The low and high pressure targets of the socket 102 can be obtained similarly from trials or in other embodiments, the user may manually select the target pressure of the socket 102, such as through the use of a digital dial. Similarly, in another embodiment of a method for controlling the volume of the volume compensation element 104, the user is able to set a pressure target or a high and low target that is comfortable such as through a digital dial, and the pump 106 is then able to maintain this pressure throughout the day by increasing or decreasing the vacuum and/or allowing the aspiration of air within the viscoelastic memory material 122.

The system provides a socket volume compensation element 104 compensates for the changing volume of the residual limb that varies the available volume in the socket, and may also provide for a negative pressure at the limb/socket interface to maintain improved suspension resulting in more consistent forces on the limb through the entire gait cycle.

In one embodiment, a user will be able to set a desired pressure for both the viscoelastic memory material 122 and the interior of the socket 102. The pump 106 maintains the desired pressures between high and low pressure targets throughout the day by increasing or decreasing the vacuum within the viscoelastic memory material 122 and the socket 102 or allowing the viscoelastic memory material 122 and the socket 102 to aspirate air through the vent 148.

In one embodiment, an algorithm can be provided to measure one or both pressures using the pressure sensors 130 and 132 at a fixed time interval. The prosthetist and/or wearer may set a comfort zone (i.e., a range of pressures) such that the pump 106 maintains a constant pressure on the residual limb when the mean or average pressure is found to be outside that zone, either high or low, and the pump 106 would automatically vent the viscoelastic memory material 122 to atmosphere (thus expanding it and accommodating for reduced residual limb volume) or pump it down (thus compressing it and accommodating for increased residual limb volume).

In one embodiment, the viscoelastic memory material 122 is an open-cell viscoelastic memory foam. In one embodiment, the viscoelastic memory material 122 includes an open-cell, flexible viscoelastic polyurethane-based foam. As used herein, "foam" is used interchangeably with the viscoelastic memory material 122. The viscoelastic memory material 122 may be made from ethylene-oxide polyether polyols, polymeric diphenylmethane diisocyanate (pMDI), water (as a blowing agent), reactive catalysts (which reduces or eliminates the chemical smell and impact on the environment), reactive colorants, surfactants, and antioxidants. In one embodiment, the viscoelastic memory material 122 is compatible with human tissue, so as not to create any undesired reactions with human tissue. This is done by employing a manufacturing method, without the use of fillers, such as melamine, antimony, auxiliary blowing agents, halogenated (bromine, chlorine, etc.) materials, or formaldehyde. The viscoelastic memory material 122 can specifically exclude the use of toluene diisocyanate, eliminating toluene diamine formation. Further, the viscoelastic memory material 122 can be manufactured to avoid the release of a detectable amount of substances into the surrounding atmosphere per evolved gas analysis (ASTME 2105).

The viscoelastic memory material 122 may have an open-cell structure to allow air permeability throughout the material to be able to be compressed under the influence of the vacuum pump 138 or pressure exerted on it by the residual limb. A suitable viscoelastic memory material 122 has a transition temperature between a fully firm state and an alternate soft state that is at or above normal body temperature. Conventional viscoelastic memory foams, such as are used for mattresses and pillows, use a lower transition temperature than body temperature to allow adaptation to human forms. However, viscoelastic memory foams used either for pillows or mattresses would have the disadvantage that these foams would lose too much resilience and not provide a sufficiently firm surface in the socket 102.

The viscoelastic memory material 122 is chosen to have a time course for rebound after compression that is greater than or equal to 1 second, for example, so that during normal gait, the volume of the material 122 remains essentially the same during the periods between stance phase when the residual limb is bearing down against the socket 102 and the swing phase, when the residual limb carries the prosthesis to the beginning of the next stance phase. The rebound of material 122 relies on the memory to provide an expansion force against the residual limb to draw in atmospheric air.

In one embodiment, a suitable compression range for the viscoelastic memory material 122 from the noncompressed state to the fully compressed state is in the range of 15-35% by volume of the normal volume and, more specifically, a range of 20-25% of the normal volume. The normal volume is the volume of the viscoelastic memory material when not exposed to a compressive force, at atmospheric pressure. The range of volume change can allow for a 2½ to 3 mm variance of the soft tissue. Accordingly, a 15 mm thick layer of viscoelastic memory material 122 is suitable to accommodate a change in diameter of the residual limb of 2½ to 3 mm. It is to be appreciated that the thickness of the viscoelastic form can be made greater or smaller depending on the diameter of the residual limb. As an alternative to having a thicker foam layer, more than one layer of foam can be utilized in the socket. For example, a first layer may be placed in the rear of the socket, while a second layer may be placed at the front of the socket, or both layers may be juxtaposed next to each other. The combined thickness of the two layers may be equal to the desired thickness to accommodate the desired change in size of the residual limb. Additionally, if more than one viscoelastic memory material is used, each material can have different resiliency properties. For example, a material with different resiliency properties can be used in different areas of the socket.

In one embodiment, the volume compensation element 104 includes a silicone pouch in which the viscoelastic memory material 122 is placed. The silicone pouch is one embodiment for creating air impermeable skin 150 next to the viscoelastic memory material 122. The interior of the pouch, and thus the viscoelastic memory material 122, is connected to the conduit 126 through which the interior of the pouch and the viscoelastic memory material 122 can be subjected to ambient atmospheric pressure via vent 148, or, alternatively, to a vacuum pump 138 through a series of valves, as described above. The pouch can be sealed to the conduit 126, to prevent the escape of pressure. The silicone pouch can be 3 mm thick and have a durometer of approximately 40 shore-A. In another embodiment, the silicone pouch can be 1.5 mm thick and have a durometer of approximately 30 shore-A.

In one embodiment, the viscoelastic memory material 122 is placed within a hard-shell cassette 152. The cassette 152 forms an outward projection of the socket 102. A hole in the socket 102 can be created to fit a viscoelastic memory material. Alternatively, the socket 102 can be manufactured with the outward projection already provided, without the need for a separate and distinct hard-shell cassette. The volume of the cassette 152 is commensurate in size with the volume of the viscoelastic memory material 122 in a fully compressed state. For donning a prosthesis incorporating the volume compensation element 104 including the viscoelastic memory material 122, the viscoelastic memory material 122 may be compressed by the pump 106 so that the residual limb will fit into the socket 102. Thereafter, the vacuum can be released (by configuring valves 136 and 138 to vent 148), thus, allowing the viscoelastic memory material 122 to expand to a volume that is in equilibrium with the force of the residual limb pushing against it.

In one embodiment, the cassette 152 hard shell is secured to the viscoelastic memory material 122 using silicone cement, so as to provide an air impermeable seal. The viscoelastic memory material 122 is then sealed from the interior of the socket 102 using, for example, a 3 mm thick sheet of silicone having a durometer of approximately 40 shore-A. In another embodiment, the viscoelastic memory material 122 is sealed using a 1.5 mm thick sheet of silicone having a durometer of approximately 30 shore-A. The silicone stretches to cover the necessary area and volume of the cassette hole in the socket and is secured at the edges by compression between the cassette 152 edge and the socket 102 proper. This prevents the silicone from contracting with the viscoelastic memory material. It also provides a complete airtight seal to maintain the vacuum suspension system in the socket 102. In other embodiments, the viscoelastic memory material 122 is placed in the silicone pouch referred to above, and then cemented to or otherwise attached to the cassette 152. In still other embodiments, silicone may be replaced by ultrasonically welded polyurethane. Additionally, the interface between the volume compensation element 104 and human tissue may include other materials to distribute load, limit abrasion, and prolong life.

The cassette 152 with the viscoelastic memory material 122 can be bolted to the socket 102 at an opening in the socket 102, and sealed using a thin layer of silicone putty to ensure an airtight seal for the vacuum maintenance of the interior of socket 102. One or more cassettes as described may be placed at one or more locations on the socket 102. Each cassette 152 having a viscoelastic memory material 122 may be connected to pump 106.

In view of the above description, the following are non-limiting examples of embodiments. Every embodiment may include one, more than one, or all of the features of every other embodiment.

Some embodiments are related to a method of compensating for variations in volume of a residual limb within a prosthesis socket. The method includes aspirating a compressible fluid into a viscoelastic memory material within an interior of a socket when a residual limb decreases in volume within the socket, wherein, as the viscoelastic memory is filled with the fluid, the viscoelastic memory material expands to compensate for the volume decrease in the residual limb.

In some embodiments, the viscoelastic memory material may expand to create vacuum within the viscoelastic memory material to draw the compressible fluid within the viscoelastic memory material as the residual limb decreases.

In some embodiments, the method may further include withdrawing the compressible fluid from the viscoelastic memory material when the residual limb volume increases within the socket.

In some embodiments, a vacuum may be created external to the viscoelastic memory material to withdraw the compressible fluid from the viscoelastic memory material In some embodiments, the method may further include sensing a pressure experienced by the viscoelastic memory material and maintaining the sensed pressure within a range between a low pressure target and high pressure target.

In some embodiments, the method may further include, when the sensed pressure is below the low pressure target, aspirating a fluid into the viscoelastic memory material and increasing the volume of the viscoelastic memory material until the sensed pressure is above the low pressure target.

In some embodiments, the method may further include, when the sensed pressure is above the high pressure target, removing a fluid from the viscoelastic memory material and decreasing the volume of the viscoelastic memory material until the sensed pressure is below the high pressure target.

In some embodiments, the method may further include sensing a pressure experienced by the viscoelastic memory material, correlating the sensed pressure to a correlated size of the viscoelastic memory material, comparing the correlated size of the viscoelastic memory material to a size target, and when the correlated size is less than the size target, aspirating a fluid into the viscoelastic memory material to increase the size of the viscoelastic memory material.

In some embodiments, the method may further include aspirating fluid through a conduit open to atmospheric air.

In some embodiments, the method may further include sensing a pressure experienced by the viscoelastic memory material, correlating the sensed pressure to a correlated size of the viscoelastic memory material, comparing the correlated size of the viscoelastic memory material to a size target, and, when the correlated size is greater than the size target, removing a fluid from the viscoelastic memory material to decrease the size of the viscoelastic memory material.

In some embodiments, the method may further include operating a vacuum pump connected to the viscoelastic memory material to remove the fluid from the viscoelastic memory material.

In some embodiments, the method may further include sensing a pressure experienced by the viscoelastic memory material, and, when the sensed pressure is below a low pressure target caused by swinging the prosthesis during a swing phase of walking, delaying aspirating a fluid into the viscoelastic memory material.

In some embodiments, the method may further include sensing a pressure experienced by the viscoelastic memory material, and, when the sensed pressure is above a high pressure target caused by standing on the prosthesis during a stance phase of walking following a swing phase, delaying removing a fluid from the viscoelastic memory material.

In some embodiments, the viscoelastic memory material may include an open cell structure, and have a transition temperature between a fully firm state and an alternate soft state that is at or above normal body temperature.

In some embodiments, the viscoelastic memory material may have predetermined time for rebound after compression that is at least one second.

In some embodiments, the method may further include sensing a pressure within an interior of the socket, and maintaining the sensed pressure between a low pressure target and a high pressure target.

Any one, more than one, or all of the described features relating to a method may be combined with every other feature.

In some embodiments, a prosthesis is disclosed. The prosthesis includes, a socket defining an interior available volume, wherein the socket has an opening for receiving a residual limb. The prosthesis includes a viscoelastic memory material placed on the socket, wherein the viscoelastic memory material is configured to create a vacuum to aspirate a compressible fluid from outside the viscoelastic memory material and decrease the available volume within the socket. The prosthesis may include a pump connected to the viscoelastic memory material, wherein the pump is configured to create a vacuum to withdraw the compressible fluid from within the viscoelastic memory material and increase the available volume within the socket.

In some embodiments, the viscoelastic memory material may be placed on a side wall of the socket.

In some embodiments, the prosthesis may further include a pressure sensor configured to measure the pressure experienced by the viscoelastic memory material.

In some embodiments, the prosthesis may further include a vent connected to the viscoelastic memory material, wherein the vent is configured to connect the viscoelastic memory material to atmospheric air.

In some embodiments, the viscoelastic memory material may include an open-cell foam.

In some embodiments, the prosthesis may further include a storage unit having a correlation table that correlates a pressure to a volume of the viscoelastic memory material.

In some embodiments, the prosthesis may further include a storage unit having a correlation table that correlates a pressure to a volume of the viscoelastic memory material for a time of a day.

In some embodiments, the viscoelastic memory material has a transition temperature between a firm state and a soft state that is at or above a normal human body temperature.

In some embodiments, the viscoelastic memory material may be placed at a rear wall of the socket.

In some embodiments, the prosthesis may further include an impermeable barrier between the viscoelastic memory material and the interior of the socket.

In some embodiments, the impermeable barrier may be a skin formed from the viscoelastic memory material.

In some embodiments, the impermeable barrier is an elastic material.

In some embodiments, the prosthesis may further include more than one viscoelastic memory materials, each viscoelastic memory material being placed at a different location on the socket.

In some embodiments, the prosthesis may further include a central processing unit configured to operate the pump, wherein the central processing unit is programmed to receive a sensed pressure, correlate a volume of the viscoelastic memory material based on the sensed pressure, determine whether the correlated volume is above or below a predetermined volume, calculate a volume difference required to achieve the predetermined volume and commands aspiration of the viscoelastic memory material when the correlated volume is below the predetermined volume and commands a pressure decrease of the viscoelastic memory material when the correlated volume is above the predetermined volume.

In some embodiments, the pump may be further connected to the interior of the socket, and the pump is configured to maintain a pressure within the interior of the socket, and maintain a pressure within the viscoelastic memory material.

In some embodiments, the viscoelastic memory material is provided in a projection provided in the socket.

In some embodiments, an opening may be provided in the sidewall of the prosthesis, a cassette configured to the shape of the viscoelastic memory material is provided over the opening and forms the sidewall of the socket, and the viscoelastic memory material is provided within the cassette.

In some embodiments, the prosthesis may further include an adaptor, a prosthetic foot, and a pylon, wherein the adaptor is rigidly attached to a base of the socket, the pump is configured to receive the adaptor at an interface configured to allow angulation of the adaptor to align the socket to a remainder of the prosthesis, and the pump is connected to a prosthetic foot via the pylon.

In some embodiments, the prosthesis may include a socket defining an interior available volume with an opening for receiving a residual limb, a viscoelastic memory material placed on the socket, wherein the viscoelastic memory material is configured to expand to reduce the available volume within the socket, and the viscoelastic memory material is in communication with ambient atmospheric pressure.

Any one, more than one, or all of the described features relating to a prosthesis may be combined with every other feature.

Following long-standing patent law, the words "a" and "an," when used in the claims or specification, denotes one or more, unless specifically noted.

While illustrative embodiments have been illustrated and described, it will be appreciated that various changes can be made therein without departing from the spirit and scope of the invention.

The invention claimed is:

1. A method of compensating for variations in volume of a residual limb within a prosthesis socket, comprising:
aspirating a compressible fluid into a viscoelastic memory foam material within an interior of a socket when a residual limb decreases in volume within the socket, wherein, as the viscoelastic memory foam material is filled with the fluid, the viscoelastic memory foam material expands to compensate for the volume decrease in the residual limb, wherein the viscoelastic memory foam material comprises an open cell structure and has a transition temperature between a firm state and a soft state that is at or above normal body temperature.

2. The method of claim 1, wherein, as the residual limb volume decreases, the viscoelastic memory foam material expands to create vacuum within the viscoelastic memory foam material to draw the compressible fluid within the viscoelastic memory material.

3. The method of claim 1, further comprising withdrawing the compressible fluid from the viscoelastic memory foam material when the residual limb volume increases within the socket.

4. The method of claim 3, wherein a vacuum is created external to the viscoelastic memory foam material to withdraw the compressible fluid from the viscoelastic memory foam material.

5. The method of claim 1, further comprising sensing a pressure experienced by the viscoelastic memory foam material, and maintaining the sensed pressure within a range between a low pressure target and a high pressure target.

6. The method of claim 5, further comprising, when the sensed pressure is below the low pressure target, aspirating a fluid into the viscoelastic memory foam material and increasing the volume of the viscoelastic memory foam material until the sensed pressure is above the low pressure target.

7. The method of claim 5, further comprising, when the sensed pressure is above the high pressure target, removing the fluid from the viscoelastic memory foam material and decreasing the volume of the viscoelastic memory foam material until the sensed pressure is below the high pressure target.

8. The method of claim 1, further comprising sensing a pressure experienced by the viscoelastic memory foam material, correlating the sensed pressure to a correlated size of the viscoelastic memory foam material, comparing the correlated size of the viscoelastic memory foam material to a size target, and, when the correlated size is less than the size target, aspirating a fluid into the viscoelastic memory foam material to increase the size of the viscoelastic memory foam material.

9. The method of claim 8, further comprising aspirating fluid through a conduit open to atmospheric air.

10. The method of claim 1, further comprising sensing a pressure experienced by the viscoelastic memory foam material, correlating the sensed pressure to a correlated size of the viscoelastic memory foam material, comparing the correlated size of the viscoelastic memory foam material to a size target, and, when the correlated size is greater than the size target, removing a fluid from the viscoelastic memory foam material to decrease the size of the viscoelastic memory foam material.

11. The method of claim 10, further comprising operating a vacuum pump connected to the viscoelastic memory foam material to remove the fluid from the viscoelastic memory foam material.

12. The method of claim 1, further comprising sensing a pressure experienced by the viscoelastic memory foam material, and, when the sensed pressure is below a low pressure target caused by swinging the prosthesis during a swing phase of walking, delaying aspirating a fluid into the viscoelastic memory foam material.

13. The method of claim 1, further comprising sensing a pressure experienced by the viscoelastic memory foam material, and, when the sensed pressure is above a high pressure target caused by standing on the prosthesis during a stance phase of walking following a swing phase, delaying removing a fluid from the viscoelastic memory foam material.

14. The method of claim 1, wherein the viscoelastic memory foam material has a predetermined time for rebound after compression that is at least one second.

15. The method of claim 1, further comprising sensing a pressure within an interior of the socket, and maintaining the sensed pressure between a low pressure target and a high pressure target.

\* \* \* \* \*